(12) United States Patent
Lai

(10) Patent No.: US 6,406,146 B1
(45) Date of Patent: Jun. 18, 2002

(54) WAVEFRONT REFRACTOR SIMULTANEOUSLY RECORDING TWO HARTMANN-SHACK IMAGES

(75) Inventor: Ming Lai, Dublin, CA (US)

(73) Assignee: Carl Zeiss, Inc., Thornwood, NY (US)

( * ) Notice: Subject to any disclaimer, the term of this patent is extended or adjusted under 35 U.S.C. 154(b) by 77 days.

(21) Appl. No.: 09/667,180

(22) Filed: Sep. 21, 2000

(51) Int. Cl.[7] ................................................. A61B 3/14
(52) U.S. Cl. ...................................................... 351/206
(58) Field of Search ................................ 351/205, 206, 351/207, 211, 212, 221, 246; 606/4, 5; 128/898

(56) References Cited

U.S. PATENT DOCUMENTS

| | | | |
|---|---|---|---|
| 5,629,765 A | 5/1997 | Schmutz | 356/121 |
| 5,777,719 A | 7/1998 | Williams et al. | 351/212 |
| 5,949,521 A | 9/1999 | Williams et al. | 351/246 |
| 6,050,687 A | 4/2000 | Bille et al. | 351/212 |
| 6,095,651 A * | 8/2000 | Williams et al. | 351/246 |

FOREIGN PATENT DOCUMENTS

| WO | 27334 | 6/1999 | G01J/1/00 |
|---|---|---|---|

OTHER PUBLICATIONS

"Objective measurement of wave aberrations of the human eye with the use of a Hartmann–Shack wave–front sensor," *J. Opt. Soc. Am. A*, vol. 11, No. 7, pp. 1949–1957, Jul. 1994.
"Aberrations and retinal image quality of the normal human eye," *J. Opt. Soc. Am. A*, vol. 14, No. 11, pp. 2873–2883, Nov., 1997.

* cited by examiner

*Primary Examiner*—George Manuel
(74) *Attorney, Agent, or Firm*—Michael B. Einschlag

(57) ABSTRACT

Wavefront refractor apparatus and method which records two Hartmann-Shack images simultaneously at different distances from the lenslet array. The two images recorded this way enable each focal spot to be associated with a lenslet forming the spot to identify "bad" spots, "ghost" spots, and to provide more accurate measurements for diverging or converging wavefronts.

16 Claims, 4 Drawing Sheets

WAVEFRONT REFRACTOR SIMULTANEOUSLY RECORDING TWO HARTMANN-SHACK IMAGES

TECHNICAL FIELD OF THE INVENTION

The present invention pertains to method and apparatus for measuring optical quality of an eye. In particular, the present invention pertains to method and apparatus which measures refractive errors of an eye based on wavefront measurement.

BACKGROUND OF THE INVENTION

As is well known, a refractor is an optical apparatus used to measure refractive errors of an eye. In particular, a wavefront refractor is a refractor based on wavefront measurement, and as is further well known, a Hartmann-Shack wavefront sensor can be used to construct such a wavefront refractor.

FIG. 2 shows a block diagram of prior art wavefront refractor 200. As shown in FIG. 2, wavefront refractor 200 comprises probe beam assembly 10, polarizing beamsplitter 20, relay optics assembly 40, and Hartmann-Shack sensor assembly 50'. As shown in FIG. 2, probe beam assembly 10 comprises a radiation source (not shown) which outputs beam of radiation 11, which beam of radiation 11 (after being redirected by turning reflector 12) is applied as input to polarizing beamsplitter 20. Beam of radiation 11 typically comprises radiation that is not detected by a patient such as, for example, infrared or near infrared radiation. The source of beam of radiation 11 may be a super-luminescent diode or a laser. The beam of radiation output from polarizing beamsplitter 20 is directed to impinge upon eye 30 to form illumination spot 32 on retina 31.

As shown in FIG. 2, radiation scattered from illumination spot 32 passes through the eye's optics (including eye lens 34 and cornea 35), and emerges as outgoing beam 33. The wavefront of outgoing beam 33 carries aberration information directly relating to the optical quality of the eye's optics. For example, for a perfect emmetropic eye without aberration error, the wavefront of outgoing beam 33 is a flat plane; for a myopic or hyperopic eye, the wavefront of outgoing beam 33 has the shape of a spherical surface; and for an eye with high order aberrations, the wavefront of outgoing beam 33 is distorted irregularly.

As shown in FIG. 2, relay optics assembly 40 relays the wavefront of outgoing beam 33 from exit pupil plane P of eye 30 to Hartmann-Shack sensor assembly 50' disposed at conjugate plane P'. As further shown in FIG. 2, Hartmann-Shack sensor assembly 50' of prior art wavefront refractor 200 comprises lenslet array 51 and CCD camera 53. The principles and design parameters used to fabricate Hartmann-Shack sensor assembly 50' are well known in the art. In accordance with the prior art design, CCD camera 53 is located at the focal plane of the lenslet elements of lenslet array 51, and prior art Hartmann-Shack sensor assembly 50' detects the wavefront of outgoing beam 33 when lenslet array 51 divides the wavefront of outgoing beam 33 into sub-apertures of the lenslets. Each lenslet forms a focal spot such as focal spot 52 on CCD camera 53, and as is well known, the pattern of focal spots carries the signature of the wavefront of the beam to be measured.

In accordance with this prior art design, output from CCD camera 53 is applied as input to analyzer 60, for example, a personal computer. Analyzer 60 then determines the x, y, z position of a centroid of each of the focal spots in accordance with any one of a number of methods that are well known to those of ordinary skill in the art. Next, analyzer 60 determines the slope of each beam segment using the coordinates of the centroids to determine the slope of a portion of the beam passing through each of the elements of lenslet array 50. Next, analyzer 60 uses any one of a number of methods that are well known to those of ordinary skill in the art to use the slopes of the beam segments to reconstruct the wavefront of beam 33 at plane P'. For example, in one such embodiment, analyzer 60 fits the slopes of the beam segments to a set of Zernike polynomials to reconstruct the wavefront of beam 33 at plane P' in accordance with the teaching of an article entitled "Objective measurement of wave aberrations of the human eye with the use of a Hartmann-Shack wave-front sensor" by J. Liang et al., *J. Opt. Soc. Am. A*, Vol. 11, No. 7, July 1994, pp. 1949–1957, and an article entitled "Aberrations and retinal image quality of the normal human eye" by J. Liang et al., *J. Opt. Soc. Am. A*, Vol. 14, No. 11, November 1997, pp. 2873–2883 (the "Liang articles"), which Liang articles are incorporated by reference herein. The wavefront of outgoing beam 33 is then reconstructed at plane P via a scale factor determined by relay optics assembly 40. A review of the Hartmann-Shack wavefront sensor, and wavefront reconstruction is found in U.S. Pat. No. 5,777,719. Finally, the refractive errors of the eye are calculated by analyzer 60 in accordance with any one of a number of methods that are well known to those of ordinary skill in the art using the reconstructed wavefront. For example, one such method is disclosed in a publication of Frey et al. on Jun. 3, 1999, WO 99/27334 entitled "Objective Measurement and Correction of Optical Systems Using Wavefront Analysis" wherein distortions of the wavefront are taken as an estimate of the aberrations, which publication is incorporated by reference herein (see also the Liang articles). An algorithm for use in analyzer 60, for example, a computer algorithm, is commercially available from, for example, Adaptive Optics Associates of Cambridge, Mass.

Comprehensive measurement of the refractive errors of the eye's optics provided by prior art wavefront refractor 200 include high order aberrations. Such comprehensive measurement of the refractive errors can be used to guide laser surgery to correct the refractive errors of the eye. Advantageously, a wavefront refractor can provide more accurate measurement of the refractive errors of an eye than a conventional auto-refractor. Consequently, a wavefront refractor may eventually be used to provide prescriptions for eyeglasses and contact lenses.

However, several problems arise in using prior art wavefront refractor 200 which includes Hartmann-Shack sensor assembly 200. A first problem arises because refractive errors of a human eye can be substantial, and as a result, wavefront distortion can be significant. For the case of a planar wavefront produced by an emmetropic eye, focal spots 52 form a grid pattern on CCD camera 53 that is identical to that of lenslet array 51. However, for a case where wavefront distortion is significant, the grid pattern of focal spots 52 may be badly distorted. This causes a need for an algorithm (used to analyze the grid pattern of focal spots) to associate each focal spot with the particular lenslet used to form the focal spot.

A second problem arises because distortion of the grid pattern of focal spots can arise from a source other than refractive error of the eye. In particular, the intensity distribution of the outgoing beam can vary significantly across the exit pupil due to a number of effects, including, for example, the scattering nature of the probe beam from the retina. In such a case, some focal spots (referred to herein as "bad"

spots) may have their centroid shifted away from their chief rays—such a shift occurs whenever the intensity distribution across a lenslet has a strong slope. This causes a need for an algorithm (used to analyze the grid pattern of focal spots) to reject these shifted or "bad" spots.

A third problem arises because unwanted trace beams, i.e., beams reflected, for example, from optics elements and/or the eye, can not always be removed. In such a case, "ghost" focal spots may appear in the grid pattern of focal spots. This causes a need for an algorithm (used to analyze the grid pattern of focal spots) to identify these ghost spots.

U.S. Pat. No. 5,629,765 (the '765 patent) discloses a spot matching technique that moves a CCD camera longitudinally, and records images in several different positions. The images are then analyzed, and the displacement of each focal spot is traced toward a lenslet. By matching each focal spot to a lenslet, the average tilt of the test beam can be determined, and the sub-aperture of each lenslet can be realigned on the CCD camera. This technique enables accurate and reliable measurement of a test beam with large overall tilt with respect to an instrument axis. However, this does not solve any of the above-identified problems with respect to measurement of refractive errors of an eye. In addition to this, camera movement is typically much slower than eye movement. As a result, a movable camera does not provide a practical solution to the problems that occur in measuring refractive errors of an eye.

SUMMARY OF THE INVENTION

Embodiments of the present invention advantageously satisfy the above-identified problems in the art, and provide method and apparatus for measuring refractive errors of an eye. Advantageously, in accordance with the present invention, embodiments of the present invention enable: (a) measurement of an eye with large refractive errors; (b) measurement of a test beam with large wavefront distortion; (c) rejection of "bad" spots and "ghost" spots; and (d) reliable measurement which is free from eye movement.

Specifically, one embodiment of the present invention is a wavefront refractor which comprises: (a) relay optics adapted to relay a wavefront of a beam emerging from an eye from a corneal plane to a conjugate plane; (b) a lenslet array disposed at the conjugate plane to intercept the relayed beam; (c) a beamsplitter disposed behind the lenslet array to split radiation transmitted by the lenslet array into first radiation and second radiation; (d) a first camera disposed to receive the first radiation at a distance from the lenslet array that is shorter than a focal length of a lenslet; and (e) a second camera disposed to receive the second radiation at a distance from the lenslet array that is longer than a focal length of the lenslet.

Detailed Description

Figure 1:
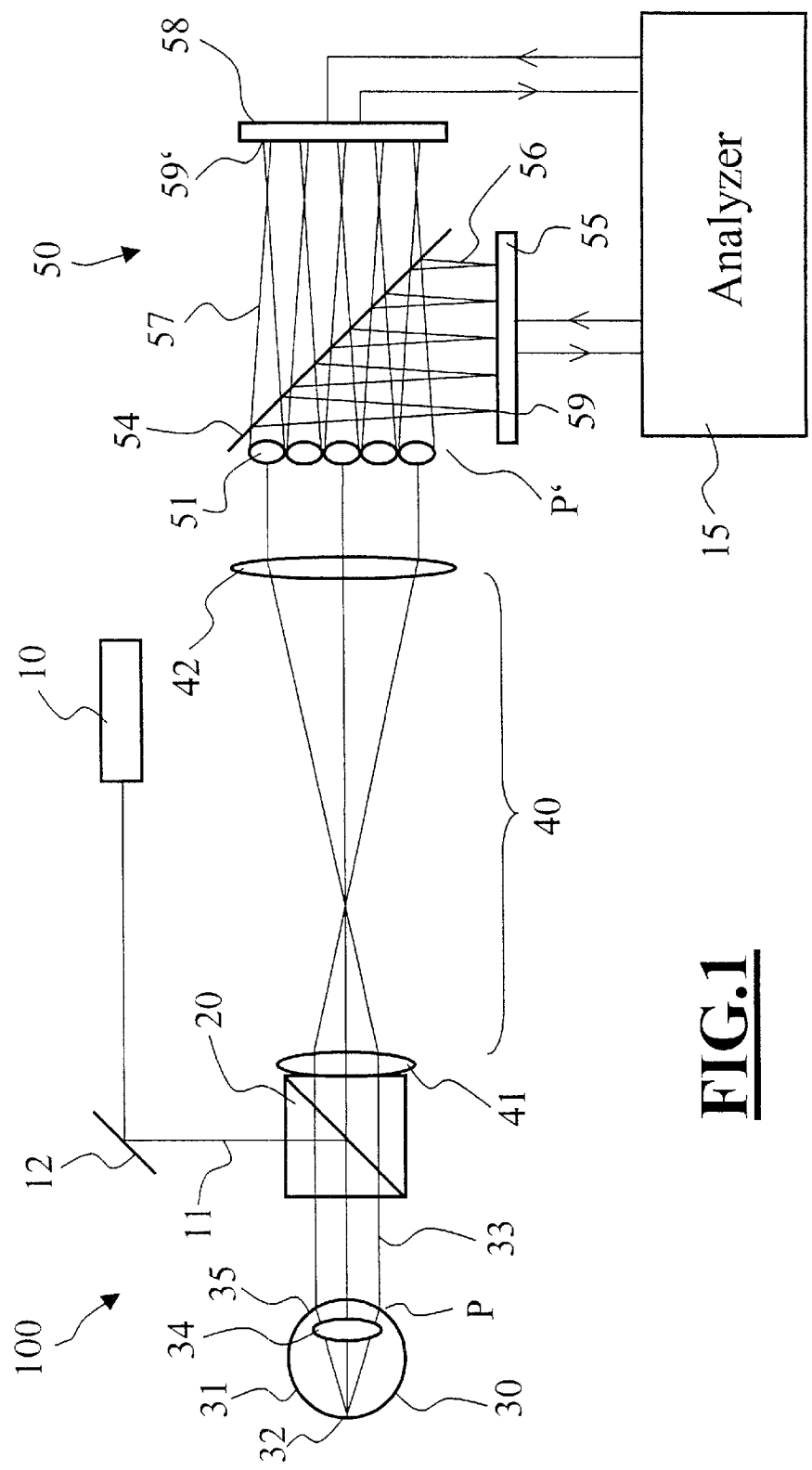
FIG. 1 shows a block diagram of a wavefront refractor that is fabricated in accordance with one embodiment of the present invention.

FIG. 1 shows a block diagram of wavefront refractor 100 that is fabricated in accordance with one embodiment of the present invention. As shown in FIG. 1, wavefront refractor 100 comprises probe beam assembly 10, polarizing beamsplitter 20, relay optics assembly 40, and Hartmann-Shack sensor assembly 50.

As shown in FIG. 1, probe beam assembly 10 comprises radiation source (not shown) which outputs beam of radiation 11, which beam of radiation 11 (after being redirected by turning reflector 12) is applied as input to polarizing beamsplitter 20. Beam of radiation 11 typically comprises radiation that is not detected by a patient such as, for example and without limitation, infrared or near infrared radiation. It is desirable to utilize a super-luminescent diode to fabricate the radiation source due to its high brightness and short coherence length. A desirable wavelength of the super-luminescent diode is in the near infrared spectrum range. However, other radiation sources may be used such as, for example and without limitation, a laser or a light emitting diode.

The beam of radiation output from polarizing beamsplitter 20 is linearly polarized radiation (polarizing beamsplitter 20 can be fabricated in accordance with a number of methods that are well known to those of ordinary skill in the art) which is directed to impinge upon eye 30 to form illumination spot 32 on retina 31. Typically, illumination spot 32 has a spot size of approximately a few hundred microns.

As shown in FIG. 1, radiation scattered from illumination spot 32 passes through the eye's optics (including eye lens 34 and cornea 35), and emerges as outgoing beam 33. The wavefront of outgoing beam 33 carries aberration information directly relating to the optical quality of the eye's optics. For example, for a perfect emmetropic eye without aberration error, the wavefront of outgoing beam 33 is a flat plane. For a myopic or hyperopic eye, however, the wavefront of outgoing beam 33 has the shape of a spherical surface. For an eye with high order aberrations, the wavefront of outgoing beam 33 is distorted irregularly. Inventive wavefront refractor 100 measures the wavefront profile of outgoing beam 33 to determine the overall refractive errors of the eye's optics.

Polarizing beamsplitter 20 only passes a portion of depolarized, outgoing beam 33 (i.e., advantageously, polarizing beamsplitter 20 rejects reflections from, among other things, eye lens 34, cornea 35, and retina 31). As shown in FIG. 1, relay optics assembly 40 comprises lens system 41 and lens system 42 (although lens system 41 and lens system 42 are each shown as a single lens, those of ordinary skill in the art will readily understand that each of lens system 41 and 42 may comprise one or more lenses). Relay optics assembly 40 relays the wavefront of outgoing beam 33 from pupil plane P of eye 30 to a conjugate plane P'. Preferably, relay optics assembly 40 has lens systems 41 and 42 installed in a confocal configuration.

As further shown in FIG. 1, Hartmann-Shack sensor assembly 50 comprises lenslet array 51, beamsplitter 54, first CCD camera 55, and second CCD camera 58. It is desired that lenslet array 51 have a sub-aperture on the order of magnitude of 1 mm, and a focal length on the order of magnitude of 10 mm. Such a lenslet array 51 is commercially available from, for example, Adaptive Optics Associates of Cambridge, Mass.

In accordance with this embodiment of the present invention, two CCD cameras 55 and 58 are both sensitive in the near infrared spectrum range, and can record two sets of focal spot patterns simultaneously. In accordance with this embodiment of the present invention, beamsplitter 54 is a broad band beamsplitter having an areal dimension of approximately 20 mm square. In a further such embodiment, beamsplitter 54 is a non-polarization dependent beamsplitter. In accordance with this embodiment of the present invention, CCD camera 55 and 58 record images in response to a signal from analyzer 75. Further, analyzer 75 may send a signal to probe 10 to synchronize operation of wavefront refractor 100 in accordance with any one of a number of methods that are well known to those of ordinary skill in the art.

In accordance with the operation of beamsplitter 54, each focal spot 59 recorded by first CCD camera 55 has a twin or paired spot 59' that is recorded by second CCD camera 58. In accordance with this embodiment of the present invention, CCD cameras 55 and 58 are disposed at different distances from lenslet array 51. As a result, the grid pattern of focal spots 59 and the grid pattern of focal spots 59' are different. In one such embodiment, the difference between the distances of CCD cameras 55 and 58 from lenslet array 51 is about a fraction of a focal length of a lenslet.

Figure 3:
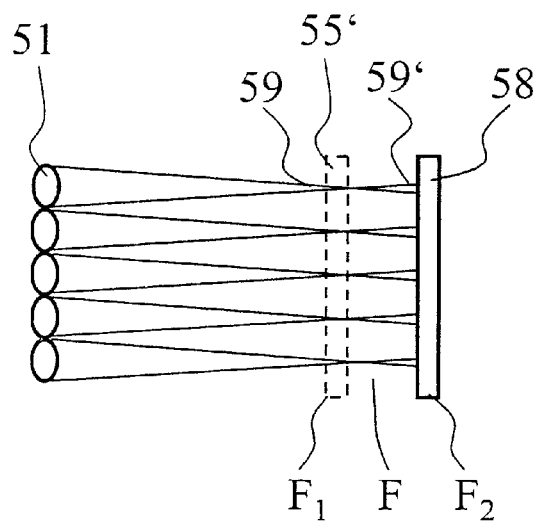
FIG. 3 shows a block diagram which illustrates how paired focal spots are recorded in an optical configuration equivalent to that shown in FIG. 1.

FIG. 3 shows a block diagram which illustrates how paired focal spots are recorded in an optical configuration equivalent to that shown in FIG. 1. The dashed line shows the equivalent position of CCD camera 55 relative to lenslet array 51. In FIG. 3, F refers to the focal plane of lenslet array 51, F1 refers to the sensor surface of first CCD camera 55, and F2 refers to the sensor surface of second CCD camera 58. In accordance with this embodiment of the present invention, the separation between F1 and F2 can be set to be approximately 10% of the focal length F of lenslet array 51. In a further embodiment, at least one of CCD cameras 55 and 58 can be movable to vary the difference between their distance to lenslet array 51 (there are many methods that are well known to those of ordinary skill in the art for moving a CCD camera under the control of, for example and without limitation, signals sent from analyzer 75). It should be clear to those of ordinary skill in the art that the focal spot pattern recorded with first CCD camera 55 will be similar to that recorded with second CCD camera 58, while the exact positions of each of paired focal spots 59 and 59' will be different in the two images.

Figure 4:
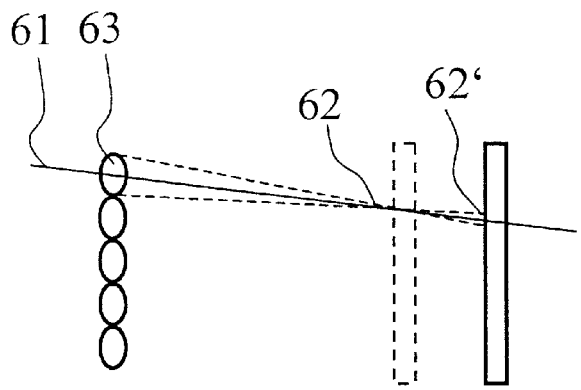
FIG. 4 shows a block diagram which illustrates how an extension line of paired focal spots can be used to identify a lenslet which formed the paired focal spots.

FIG. 4 shows a block diagram which illustrates how an extension line of paired focal spots can be used to identify a lenslet which formed the paired focal spots. In accordance with this embodiment of the present invention, after focal spot patterns are recorded with first CCD camera 55 and second CCD camera 58, an algorithm in analyzer 75 determines the centroid positions of each focal spot in accordance with any one of a number of methods that are well known to those of ordinary skill in the art. A further algorithm in analyzer 75 pairs focal spots 62 and 62' from a grid pattern recorded on CCD cameras 55 and 58, respectively, and forms a straight line (extension line 61) passing through the spots in accordance with any one of a number of methods that are well known to those of ordinary skill in the art. Since the two sets of focal spot patterns are similar to each other, paired focal spots will have a similar relative position in the two focal spot patterns, and will generally be the closest spots to each other when the two spot patterns are overlaid. Analyzer 75 uses this fact to pair focal spots using any one of a number of methods that are well known to those of ordinary skill in the art. Analyzer 75 then determines the intercept of extension line 61 and lenslet array 51 in accordance with any one of a number of methods that are well known to those of ordinary skill in the art, and determines the distance between that intercept and the center of the lenslet in accordance any one of a number of methods that are well known to those of ordinary skill in the art. The center of the lenslets in lenslet array are either predetermined, or determined by a calibration procedure and entered into analyzer 75.

If focal spots 62 and 62' were formed by a beam that was uniform across, for example, lenslet 63, then extension line 61 (formed from paired focal spots 62 and 62') should pass through the center of lenslet 63. In accordance with one embodiment of the present invention, a tolerance can be preset (or entered by a user in response to a request for input from analyzer 75) in the analysis routines of analyzer 75. Then, focal spots 62 and 62' can be identified as good spots, and can be associated with lenslet 63 within the analysis routines of analyzer 75, if extension line 61 deviates by less than the preset tolerance from the center of associated lenslet 63. Advantageously in accordance with this embodiment of the present invention, this association can be achieved reliably even though the focal spots patterns recorded may have significant distortion.

Figure 5:
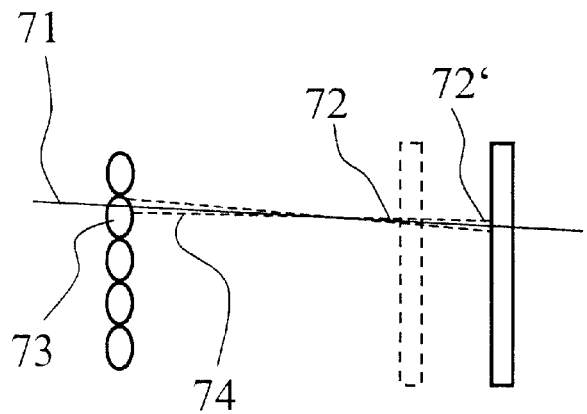
FIG. 5 shows a block diagram which illustrates how an extension line of paired focal spots can be used to identify "bad" focal spots.

FIG. 5 shows a block diagram which illustrates how extension line 71 formed from paired focal spots 72 and 72' can be used to identify that focal spots 72 and 72' are "bad". Whenever the intensity distribution across lenslet 73 varies significantly, the centroid of each focal spot 72 or 72' may not lie on the chief ray which passes through the center of lenslet 73 and the focal point of the beam incident onto lenslet 73. In such a case, extension line 71 formed from paired focal spots 72 and 72' will deviate from the center of associated lenslet 73. In accordance with one embodiment of the present invention, a tolerance can be preset (or entered by a user in response to a request for input from analyzer 75) in the analysis routines of analyzer 75, and focal spots 72 and 72' can be identified as "bad" spots, if the deviation is greater than the preset tolerance.

Figure 6:
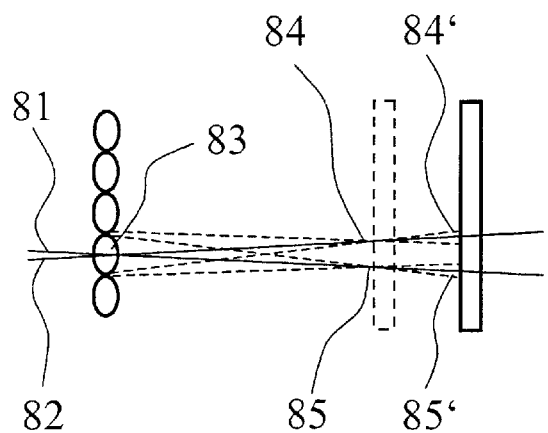
FIG. 6 shows a block diagram which illustrates how an extension line of paired focal spots can be used to identify "ghost" spots, i.e. spots produced by unwanted trace beams.

FIG. 6 shows a block diagram which illustrates how extension line 82 formed from paired focal spots 84 and 84' and extension line 81 formed from paired focal spots 85 and 85' can be used to identify "ghost" spots, i.e. spots produced by unwanted trace beams. Whenever any unwanted beam arising, for example, due to reflection from optics or the subject eye enters Hartmann-Shack sensor assembly 50, the unwanted beam forms ghost spots. In such a case, two extension lines 81 and 82 may be associated with a single lenslet 83; where one extension line is formed from a pair of good focal spots, and another extension line is formed from a pair of ghost spots. The ghost spots, for example, focal spots 84 and 84', should be rejected by computer algorithm from further processing. It is expected that, as between a "good" spot and a "ghost" spot, the "ghost" spot will deviate further from the regular focal spot pattern than the "good"

spot in terms of brightness and/or position. This deviation (for example and without limitation, in terms of brightness and/or position) may be computed in accordance with any one of a number of methods that are well known to those of ordinary skill in the art. When the deviation of one of the spots exceeds a predetermined amount in brightness and/or position, it may be rejected as being a "ghost" spot. However, there may be ambiguous cases where a spot may exceed one of the criteria but not another, if two are used, or where both spots exceed one or more of the criteria. In such a case, it is better to omit both the "good" spot and the "ghost" spot rather than using a bad data point.

Figure 7:
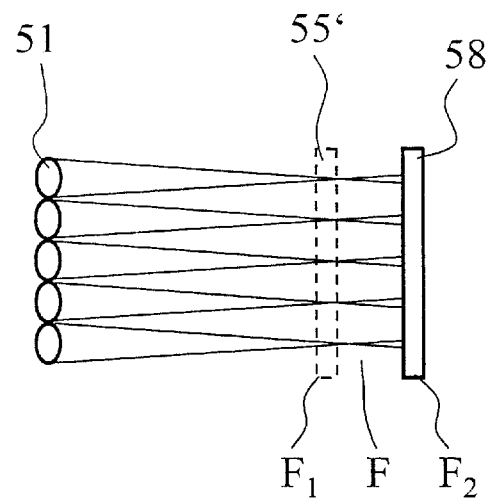
FIG. 7 shows a block diagram which illustrates that a Hartmann-Shack image taken by one CCD camera that is closer to a lenslet array than a second CCD camera can be used to obtain better measurement of a converging wavefront.

FIG. 7 shows a block diagram which illustrates that a Hartmann-Shack image taken by CCD camera 55 that is closer to lenslet array 51 than CCD camera 58 can be used to obtain better measurement of a converging wavefront. Whenever outgoing beam 33 of FIG. 1 is from a myopic eye, outgoing beam 33 has a converging wavefront. In such a case, the focal points of the converging wavefront will be located in front of focal plane F of lenslet array 51. Therefore, a Hartmann-Shack image obtained from first CCD camera 55 will have a sharper focal spot image than that obtained from second CCD camera 58. Thus, wavefront measurement based on a Hartmann-Shack image obtained from first CCD camera 55 can provide better accuracy than wavefront measurement based on a Hartmann-Shack image obtained from second CCD camera 58. Hence, in one embodiment, analyzer 75 determines whether the wavefront is converging. If the wavefront is converging, wavefront measurement results obtained from first CCD camera 55 can be used in further analysis. Analyzer 75 can determine whether the wavefront is converging by receiving user input (in accordance with any one of a number of methods that are well known to those of ordinary skill in the art) which indicates, for example, that the eye is myopic. In addition, analyzer 75 can determine the overall area of the focal spots in the Hartmann-Shack image in accordance with any one of a number of methods that are well known to those of ordinary skill in the art, and compare it with a predetermined area expected for a planar wavefront (the overall area of the Hartmann-Shack image is smaller for a converging wavefront than that for a planar wavefront).

Figure 8:
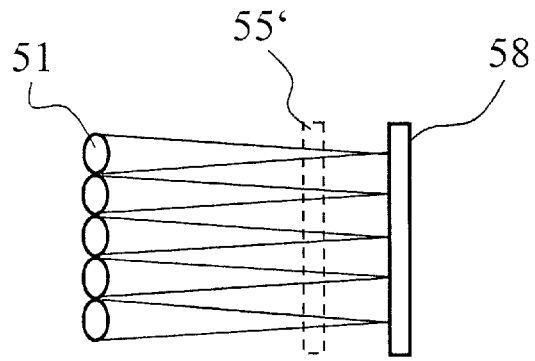
FIG. 8 shows a block diagram which illustrates that a Hartmann-Shack image taken by a second CCD camera that is farther from a lenslet array than a first CCD camera can be used to obtain better measurement of a diverging wavefront.

FIG. 8 shows a block diagram which illustrates that a Hartmann-Shack image taken by CCD camera 58 that is farther from a lenslet array than CCD camera 55 can be used to obtain better measurement of a diverging wavefront. Whenever outgoing beam 33 of FIG. 1 is from a hyperopic eye, outgoing beam 33 has a diverging wavefront. In such a case, the focal points of the diverging wavefront will located behind focal plane F of lenslet array 51. Therefore, a Hartmann-Shack image obtained from second CCD camera 58 will have a sharper focal spot image than that obtained from first CCD camera 55. Thus, wavefront measurement based on a Hartmann-Shack image obtained from second CCD camera 58 can thus provide better accuracy than wavefront measurement based on a Hartmann-Shack image obtained from first CCD camera 55. Hence, in one embodiment, analyzer 75 determines whether the wavefront is diverging. If the wavefront is diverging, wavefront measurements results obtained from second CCD camera 58 can be used in further analysis. Analyzer 75 can determine whether the wavefront is diverging by receiving user input (in accordance with any one of a number of methods that are well known to those of ordinary skill in the art) which indicates, for example, that the eye is hyperopic. In addition, analyzer 75 can determine the overall area of the focal spots in the Hartmann-Shack image in accordance with any one of a number of methods that are well known to those of ordinary skill in the art, and compare it with a predetermined area expected for a planar wavefront (the overall area of the Hartmann-Shack image is larger for a diverging wavefront than that for a planar wavefront).

In accordance with one embodiment of the present invention, the relative positions of CCD cameras 55 and 58 can be varied to obtain a sharper image for either of the above-described cases.

In accordance with one inventive technique of using the embodiment shown in FIG. 1, for a wavefront having relatively little distortion (i.e., defined as a case where the wavefront is close enough to being planar that the focal spots can be associated with their lenslets without confusion), the images obtained by CCD cameras 55 and 58 are substantially identical in terms of focal spot position, and either image can be used to reconstruct the wavefront of the beam in the same manner used to analyze a conventional Hartmann-Shack image (see the Background of the Invention). Although averaging the results of the reconstruction for the two images may improve the accuracy of the final result, it is not necessary to do so. In accordance with the one inventive technique of using the embodiment shown in FIG. 1, for a wavefront having relatively high distortion (i.e., defined as a case where the wavefront is far enough from being planar to introduce much uncertainty in associating focal spots with a lenslet), the images obtained by CCD cameras 55 and 58 are different in terms of focal spot position. In accordance with this inventive technique, focal spots can be identified as: (a) "good" spots as was described in detail above (good spots, also termed analysis spots, can be used for further processing); (b) "bad" spots as was described in detail above (bad spots, also termed rejected spots, can be excluded from further processing); and (c) "ghost" spots as was described in detail above (ghost spots, also termed rejected spots, can be excluded from further processing). Then, using the good spots, either image can be used to reconstruct the wavefront of the beam in the same manner used to analyze a convention Hartmann-Shack image. Although averaging the results of the reconstruction for the two images may improve the accuracy of the final result, it is not necessary to do so.

Figure 2:
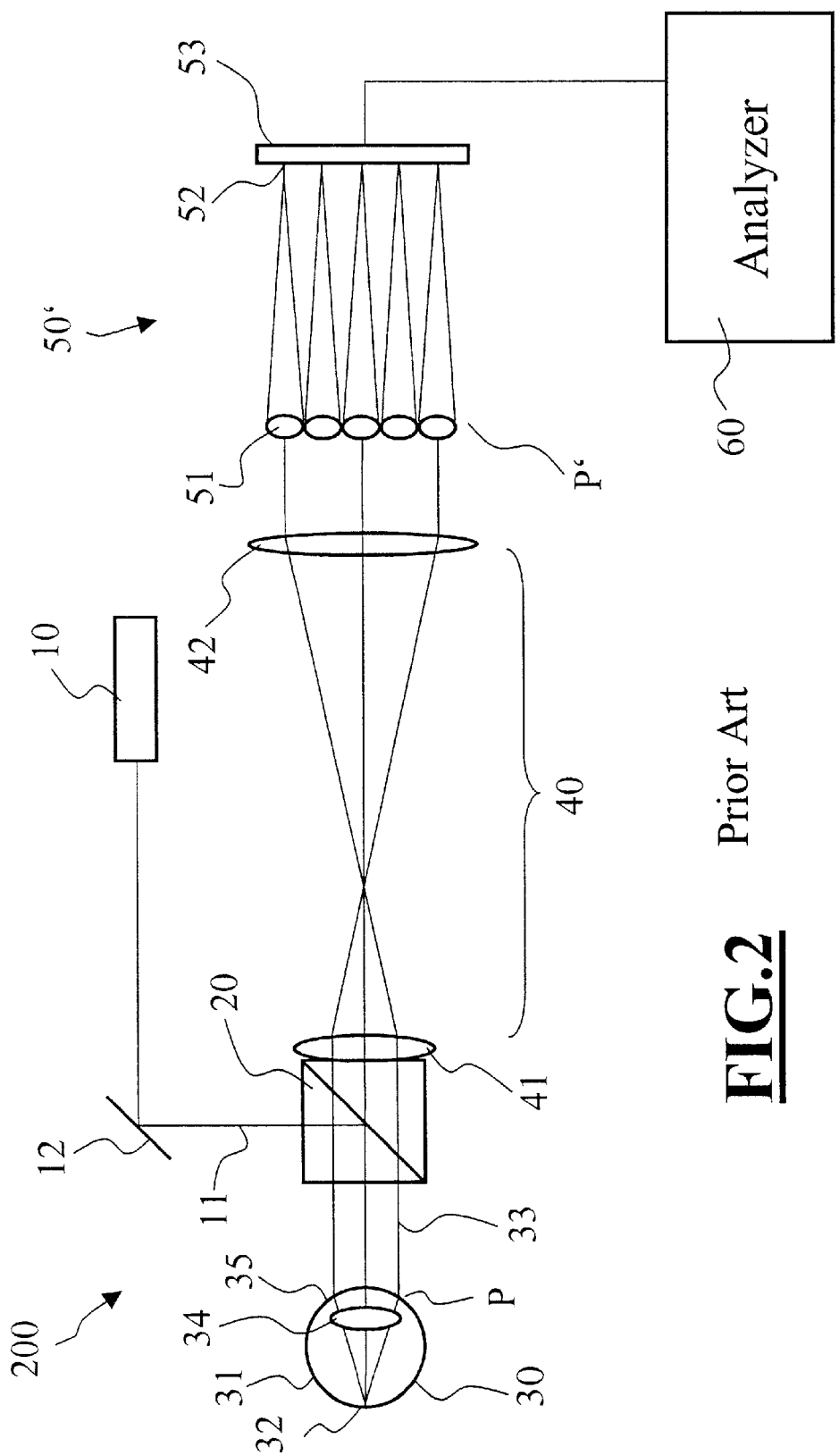
FIG. 2 shows a block diagram of a prior art wavefront refractor.

For use in measuring refractive errors of an eye, a wavefront refractor is expected to measure a wavefront in a range from about −15 diopters converging to about+15 diopters diverging. Advantageously, the embodiment shown in FIG. 1 (with first CCD camera 55 and second CCD camera 58) helps to obtain more accurate measurements over such a large dynamic range than the prior art configuration shown in FIG. 2. In addition, since eye movement limits the data acquisition time of an eye measurement to a fraction of a second, embodiments of the present invention which record two Hartmann-Shack images simultaneously make it feasible to obtain quick and accurate measurements.

Since precise alignment and calibration are critical for obtaining accurate measurements using wavefront refractor 100 shown in FIG. 1, the mechanical stability of alignment between first CCD camera 55 and second CCD camera 58 is important. For this reason, a modular package for fabricating Hartmann-Shack sensor assembly 50 shown in FIG. 1 is desirable.

Those skilled in the art will recognize that the foregoing description has been presented for the sake of illustration and description only. As such, it is not intended to be exhaustive or to limit the invention to the precise form disclosed. For example, although embodiments of the present invention were described as utilizing CCD cameras, the present invention is not limited to the use of CCD cameras and includes embodiments utilizing other types of recording devices or cameras that are sensitive to radiation used to provide the probe beam.

What is claimed is:

1. A wavefront refractor which comprises:

relay optics adapted to relay a wavefront of a beam emerging from an eye from a corneal plane to a conjugate plane;

a lenslet array disposed at the conjugate plane to intercept the relayed beam;

a beamsplitter disposed behind the lenslet array to split radiation transmitted by the lenslet array into first radiation and second radiation;

a first camera disposed to receive the first radiation at a distance from the lenslet array that is shorter than a focal length of a lenslet; and a second camera disposed to receive the second radiation at a distance from the lenslet array that is longer than a focal length of the lenslet.

2. The wavefront refractor of claim 1 wherein the relay optics comprises a pair of lenses disposed in a confocal configuration.

3. The wavefront refractor of claim 1 which further comprises a source of radiation that is directed to impinge upon, and be scattered by a retina of the eye, to form the emerging beam.

4. The wavefront refractor of claim 1 wherein the beam has a wavelength in the near infrared spectrum range.

5. The wavefront refractor of claim 1 wherein the lenslet array has a sub-aperture on the order of magnitude of 1 mm.

6. The wavefront refractor of claim 1 wherein the lenslet array has a plurality of lenslet elements, each having a focal length on the order of magnitude of 10 mm.

7. The wavefront refractor of claim 1 wherein the beamsplitter is a broad band beamsplitter having a dimension approximately 20 mm square.

8. The wavefront refractor of claim 1 wherein the first and second cameras are CCD cameras that are sensitive in the near infrared spectrum range.

9. A method for measuring refractive errors of an eye which comprises the steps of:

irradiating a retina of the eye with radiation from a probe beam;

relaying a beam emerging from the eye from a corneal plane to a conjugate plane;

wherein a lenslet array is disposed at the conjugate plane to intercept the relayed beam, a beamsplitter is disposed behind the lenslet array to split radiation transmitted by the lenslet array into first radiation and second radiation, a first camera is disposed to receive the first radiation at a distance from the lenslet array that is shorter than a focal length of a lenslet; and a second camera is disposed to receive the second radiation at a distance from the lenslet array that is longer than a focal length of the lenslet; and recording a first camera image and a second camera image simultaneously.

10. The method of claim 9 which further comprises the step of analyzing the first camera image and the second camera image to identify paired focal spots.

11. The method of claim 10 which further comprises the step of analyzing the paired focal spots to determine analysis spots.

12. The method of claim 11 which further comprises the step of analyzing the paired focal spots to determine rejected spots.

13. The method of claim 12 which further comprises the step of analyzing the analysis spots after excluding the rejected spots for at least one of the first camera image and the second camera image.

14. The method of claim 13 which further comprises the step of averaging results obtained from analyzing the first camera image and the second camera image.

15. The method of claim 11 wherein the step of analyzing the paired focal spots comprises forming a straight line passing through the spots, and determining its intercept with the lenslet array.

16. The method of claim 15 which further comprises the step of determining a distance between a center of a lenslet and the intercept.

* * * * *